US005747324A

United States Patent [19]

Mazzara et al.

[11] Patent Number: 5,747,324

[45] Date of Patent: May 5, 1998

[54] SELF-ASSEMBLED, DEFECTIVE, NON-SELF-PROPAGATING LENTIVIRUS PARTICLES

[75] Inventors: Gail P. Mazzara, Winchester; Bryan Roberts, Cambridge; Dennis L. Panicali, Acton; Linda R. Gritz, Somerville, all of Mass.; Virginia Stallard, Sequim, Wash.; Anna Mahr, Natick, Mass.

[73] Assignee: Therion Biologics Corporation, Cambridge, Mass.

[21] Appl. No.: 994,171

[22] Filed: Dec. 21, 1992

Related U.S. Application Data

[63] Continuation of Ser. No. 360,027, Jun. 1, 1989, abandoned, which is a continuation-in-part of Ser. No. 205,454, Jun. 10, 1988, abandoned.

[51] Int. Cl.$^6$ .......................... C12N 15/86; C12N 15/63; A61K 39/21; C07K 14/155

[52] U.S. Cl. ........................ 435/236; 435/69.1; 435/69.3; 435/172.3; 435/320.1; 930/221

[58] Field of Search ................................ 435/236, 320.1, 435/69.1, 69.3, 172.3; 930/221

[56] References Cited

U.S. PATENT DOCUMENTS

| | | | |
|---|---|---|---|
| 4,603,112 | 7/1986 | Paoletti et al. | 435/235.1 |

FOREIGN PATENT DOCUMENTS

| | | |
|---|---|---|
| A1 0243029 | 10/1987 | European Pat. Off. . |
| 0245136 | 11/1987 | European Pat. Off. . |
| A1 0302801 | 2/1989 | European Pat. Off. . |
| 2181435 | 4/1987 | United Kingdom . |
| WO87/02038 | 4/1987 | WIPO . |
| WO 88/02026 | 3/1988 | WIPO . |
| WO 88/03562 | 5/1988 | WIPO . |
| WO 88/03563 | 5/1988 | WIPO . |

OTHER PUBLICATIONS

Fields, B.N. et al, Eds. *Fundamental Virology*, 2nd Ed. New York: Raven Press, 1991, pp. 15, 92–93, 177.

K.L. Burke et al. (1988) Nature 332:81–82.

B.E. Clarke et al. (1988) J. Gen. Virol. 69:2313–2325.

Haffar et al., J. Virol. 64(6):2653–2659 (1990).

Hu, S. et al., *Nature* 320:537–540 (1986).

Chakrabarti, S. et al., *Nature* 320:535–537 (1986).

Kieny, M.P. et al., *Biotechnology*, 4:790–795 (1986).

Zarling, J.M. et al., *Nature* 323:344–346 (1986).

Hu, S. et al., *Nature* 328:721–723 (1987).

Zagury, D. et al., *Nature* 326:249–250 (1987).

Zagury, D. et al., *Nature* 332:728–731 (1988).

G.L. Smith and B. Moss, *Gene* 25:21–28 (1983).

Daniel, M.D. et al., *Science* 228:1201–1204 (1985).

D. Panicali and E. Paoletti, *Proc. Natl. Acad. Sci. USA* 79:4927–4931 (1982).

Panicali, D. et al., *Proc. Natl. Acad. Sci. USA* 80:5364–5368 (1983).

Letvin, N.L. et al., *Science* 230:71–73 (1985).

Franchini, G. et al., *Nature* 328:539–543 (1987).

H.W. Kestler, III et al., *Nature* 331:619–621 (1988).

Naidu, Y.M. et al., *J. Virol.* 62:4691–4696 (1988).

Perkus, M.E. et al., *Science* 229:981–984 (1985).

Chakrabarti, S. et al., *Mol. Cell. Biol.* 5:3403–3409 (1985).

Bosch, M.L. et al., *Science* 244:694–697 (1989).

Gowda, S.D. et al., *J. Biol. Chem.* 264:8459–8460 (1989).

Rautmann, G. et al., *AIDS Res. Hum. Retroviruses* 5:147–157 (Apr. 1989).

Gowda, S.D. et al., *J. Virol.* 63:1451–1454 (Mar. 1989).

Popov, S.A. et al., *Mol. Gen. Mikrobiol. Virusol.* 9:36–39 (Sep. 1988).

Flexner, C. et al., *Virology* 166:339–349 (Oct. 1988).

Mazzara, G. et al. in *Modern Approaches to Vaccines*, Cold Spring Harbor Laboratory, New York (1986).

Gheysen et al. in *Modern Approaches to New Vaccines*, Cold Spring Harbor Laboratory, New York, Sep. 14–18, 1988 Abstract No. 72.

*Primary Examiner*—Mindy Fleisher
*Assistant Examiner*—Johnny F. Railey, II
*Attorney, Agent, or Firm*—Sewall P. Bronstein; Ronald I. Eisenstein; David S. Resnick

[57] ABSTRACT

The present invention provides recombinant DNA viral vectors which co-express lentivirus genes encoding structural and enzymatic polypeptides capable of assembling into defective nonself-propagating viral particles. The viral DNA vectors as well as the viral particles can be used as immunogens and for targeted delivery of heterologous gene products and genes.

18 Claims, 10 Drawing Sheets

GENOMIC COMPARISON

SELF-ASSEMBLED, DEFECTIVE, NON-SELF-PROPAGATING LENTIVIRUS PARTICLES

RELATED APPLICATION

This is a continuation of application Ser. No. 07/360,027 filed on Jun. 1, 1989, now abandoned, Application Ser. No. 07/360,027 is a Continuation-in-part of U.S. patent application Ser. No. 205,454, filed Jun. 10, 1988 now abandoned.

This invention was made with Government support under NIH No. AI26507. The Government has certain rights in this invention.

BACKGROUND

Vaccination has played a key role in the control of viral diseases during the past 30 years. Vaccination is based on a simple principle of immunity: once exposed to an infectious agent, an animal mounts an immune defense that protects against infection by the same agent. The goal of vaccination is to induce the animal to mount the defense prior to infection. Conventionally, this has been accomplished through the use of live attenuated or killed forms of the virus as immunogens. The success of these approaches in the past has been due in part to the presentation of native antigen and the ability of attenuated virus to elicit the complete range of immune responses obtained in natural infection. However, conventional vaccine methodologies have always been subject to a number of potential limitations. Attenuated strains can mutate to become more virulent or non-immunogenic; improperly inactivated vaccines may cause the disease that they are designed to prevent.

Recombinant DNA technology offers the potential for eliminating some of the limitations of conventional vaccines, by making possible the development of vaccines based on the use of defined antigens, rather than the intact infectious agent, as immunogens. These include peptide vaccines, consisting of chemically synthesized, immunoreactive epitopes; subunit vaccines, produced by expression of viral proteins in recombinant heterologous cells; and the use of live viral vectors for the presentation of one or a number of defined antigens.

Both peptide and subunit vaccines are subject to a number of potential limitations. A major problem is the difficulty of ensuring that the conformation of the engineered proteins mimics that of the antigens in their natural environment. Suitable adjuvants and, in the case of peptides, carrier proteins, must be used to boost the immune response. In addition, these vaccines elicit primarily humoral responses, and thus may fail to evoke effective immunity.

Some of the problems associated with the use of peptides and subunit vaccines can be overcome through the use of live viral vectors to present heterologous antigens. A number of viral vectors, including retro-, adeno-, herpes-, and poxviruses (Cepko et al., 1984. *Cell* 37:1053–1062; Morin et al., 1987. *Proc. Natl. Acad. Sci. USA* 84:4626–4630; Lowe et al., 1987. *Proc. Natl. Acad. Sci. USA* 84:3896–3900; Panicali & Paoletti, 1982. *Proc. Natl. Acad. Sci. USA* 79:4927–4931 Mackett et al., 1982. *Proc. Natl. Acad. Sci. USA* 79:7415–7419) have been developed; the greatest effort has been concentrated on the development of vaccinia virus, an orthopox virus, as an infectious eukaryotic cloning vector for this purpose (Paoletti and Panicali, U.S. Pat. No. 4,603, 112). Heterologous genes, including those encoding antigens from a variety of pathogens, have been expressed in the vaccinia vector system. In all cases, the foreign gene product expressed by the recombinant vaccinia virus was similar or identical to the gene product synthesized under native conditions. In some instances, vaccination of laboratory animals with recombinant vaccinia viruses has protected these animals against challenge with the correlate pathogens (Paoletti et al., 1984. *Proc. Natl. Acad. Sci. USA* 81:193–197; Kieny et al. 1984. *Nature* 312:163–166; Alizon et al., 1984. *Nature* 312: 757–760; Boyle et al. 1985. *Gene* 35: 169–177; Yilma et al. 1988. *Science* 242:1058–1061).

Recombinant approaches have been used in attempts to develop vaccines against diseases for which no vaccine currently exists, or for which conventional vaccine approaches are less desirable. For example, since the human immunodeficiency virus (HIV) was first identified as the etiologic agent of Acquired Immunodeficiency Disease Syndrome (AIDS), (Barre-Sinoussi et al., 1983. *Science* 220:868; Levey et al., 1984. *Science* 225:840; Gallo et al., 1984. *Science* 224:500), considerable effort has been directed towards the development of a safe and effective vaccine. These efforts have relied upon a broad spectrum of strategies, ranging from the use of small synthetic peptides to whole inactivated virus as immunogen.

The emergence of the AIDS pandemic may represent the most serious public health threat of the twentieth century. Since the recognition of AIDS in 1981, extensive research has resulted in substantial advances in the understanding of the disease. The causative virus, (HIV), has been identified and the major routes of transmission have been shown to be sexual contact and exchange of blood products (Curran et al. 1985. *Science* 229:1352). The nucleotide sequences of the genomes of many isolates of HIV have been determined and the molecular biology of the virus is under intensive investigation. However, much work remains to be done in elucidating viral replication in infected individuals and its role in the pathogenesis of disease.

The human immunodeficiency viruses, HIV-1 and HIV-2, are members of the lentivirus subclass of retroviruses (Gonda et al., 1985. *Science* 227:173; Sonigo et al., 1985. *Cell* 42:369). Also in this subclass are the related simian immunodeficiency viruses (SIV; Daniel et al., 1985. *Science* 228: 1201). The human and simian immunodeficiency viruses share similar morphology. The virus particles contain an inner core comprised of capsid proteins (encoded by the viral gag gene) that encase the viral RNA genome (Rabson & Martin, 1985. *Cell* 40:477). The central core is surrounded by a lipid envelope that contains the virally-encoded envelope glycoproteins. Virus-encoded enzymes required for efficient replication, such as the reverse transcriptase and integrase (encoded by the pol gene), are also incorporated into the virus particle.

Nucleotide sequence analysis of HIV and SIV genomes has shown that these viruses also share a distinctive genome organization (FIG. 1), as well as considerable DNA sequence homology (Chakrabarti, et al., 1987. *Nature* 328:543; Franchini et al., 1987. *Nature* 328:539). The approximately 10 kb genome comprises the flanking long terminal repeat (LTR) sequences that contain regulatory segments for viral replication, as well as the gag, pol, and env genes coding for the core proteins, the reverse transcriptase-protease-endonuclease, and the envelope glycoproteins, respectively. These viruses also contain at least six additional genes, some of which have known regulatory functions.

Finally, the human and simian immunodeficiency viruses share common biological properties, including cytopathic effect, tropism for CD4-bearing cells, and, most importantly, the ability to induce long term persistent infection and chronic immunodeficiency disease in humans (HIV-1 and HIV-2) or non-human primates (SIV). The similarities between HIV and SIV have led to the development of SIV infection of rhesus macaque monkeys as a model system for the study of pathogenesis and prevention of immunodeficiency disease.

There are obvious difficulties with the use of whole virus for an HIV vaccine. The fear that an attenuated virus could revert to virulence, and the danger of incomplete inactivation of killed virus preparations, together with the reluctance to introduce the HIV genome into seronegative individuals have argued against the uses of live attenuated or killed HIV vaccines for the prevention of infection.

AIDS vaccines now under consideration span the range of possible recombinant approaches; many, though not all, rely upon the use of all or part of the envelope glycoprotein as immunogen. However, many of the recombinant vaccines tested to date have yielded disappointing results. For example, when a subunit vaccine consisting of envelope glycoprotein gp120 was used to immunize chimpanzees, specific humoral immune responses to HIV capable of neutralizing the virus in vitro were elicited; however, the immunization failed to protect the animals from HIV infection (Berman et al., 1988. *Proc. Natl. Acad. Sci. USA.* 85:5200–5204). The use of live recombinant vaccinia virus expressing the HIV envelope glycoproteins as a vaccine for the prevention of HIV infection in chimpanzees has also been unsuccessful. Infection of susceptible cells with these recombinants results in the normal synthesis, glycosylation, processing, and membrane transport of the envelope polypeptide (Chakrabarti et al., 1986. *Nature* 320:535; Hu et al., 1986. *Nature* 320:537). The gene product can be recognized by serum antibodies from patients with AIDS, and has been shown to mediate syncytia formation with cells expressing the CD4 cell surface epitope (Lifson et al., 1986. *Nature* 323:725). Vaccination of several species with these recombinants has elicited strain-specific humoral immune responses as well as cell-mediated responses (Hu, et al., 1986 *Nature* 320:537; Chakrabarti, et al., 1986. *Nature* 320:535; Kieny et al., 1986. *Biotechnology* 4:790; Zarling et al., 1986. *Nature* 323:344; Hu et al., 1987. *Nature* 328: 721; Zagury et al., 1987. *Nature* 326:249; Zagury et al., 1988. *Nature* 322:728). Nevertheless, despite these immune responses, these vaccines failed to protect chimpanzees from infection by HIV (Hu et al., 1987. *Nature* 328:721). The failure of these initial vaccinia-based vaccines may be attributed to a variety of factors. The immunogenicity of the vaccinia recombinants may not have been optimal; in fact, the recombinants elicited low antibody titers in chimpanzees. Certainly, the fact that these vaccines induce expression of only a single HIV-1 polypeptide suggests that they may not have the maximum potential for stimulating protective immune responses. Furthermore, the use of chimpanzees to evaluate AIDS vaccines is itself questionable, as chimpanzees, although they can be infected with HIV, do not develop AIDS (Alter et al., 1984. *Science* 226:549; Fultz et al., 1986. *J. Virol.* 58:116).

The potential drawback to any of the recombinant approaches to AIDS vaccine development is that they have relied upon the use of a single HIV antigen, most usually the envelope glycoprotein, as immunogen. The success in the past of traditional vaccine approaches for other diseases (such as polio, measles, mumps, and rabies), which are based on the use of whole virus, either live attenuated or killed, as immunogens, suggests that antigen presentation is of paramount importance in eliciting protective immune responses.

Advances in recombinant DNA technology may make it possible to use heterologous expression systems for the synthesis not only of individual antigens, but also of defective, non-self propagating, virus-like particles. It has been demonstrated that capsid proteins of certain viruses can assemble into particles morphologically and immunologically similar to the corresponding virus. For example, the P1 precursor of several picornaviruses synthesized in vitro can be processed into individual capsid proteins which then assemble into immunoreactive virion-like particles (Nicklin et al. 1986. *Biotechnology* 4:33; Palmenberg et al., 1979. *J. Virol.* 32:770; Shih et al., 1978. *Proc. Natl. Acad. Sci. USA* 75:5807; Hanecak et al., 1982. *Proc. Natl. Acad. Sci. USA* 79:3973; Grubman et al., 1985. *J. Virol.* 56:120). Self-assembly of capsid proteins expressed in vivo in several recombinant expression systems has also been reported. For example, when human hepatitis B surface antigen is expressed in yeast cells, the polypeptide assembles into particles similar in appearance to those isolated from human plasma (Valenzuela et al., 1982. Nature 298: 347); these particles stimulate anti-hepatitis B antibody production in several species and can protect chimpanzees from virus challenge (McAleer et al., 1984. *Nature* 307:178). In another example, it was shown that coexpression of canine parvovirus (CPV) capsid proteins VP1 and VP2 in murine cells transformed with a bovine papilloma virus/CPV recombinant plasmid resulted in the formation of self-assembling virus-like particles (Mazzara et al., 1986. in *Modern Approaches to Vaccines*, Cold Spring Harbor Laboratory, N.Y.; R. M. Chanock and R. A. Lerner, eds. pp. 419–424; Mazzara et al., U.S. patent application Ser. No. 905,299, filed Sep. 8, 1986); when used to vaccinate susceptible dogs, these empty capsids elicited immune responses capable of protecting against CPV challenge. Finally, it has been shown that the HIV-1 p55gag precursor polypeptide expressed in *Spodoptera frugiperda* cells using a baculovirus expression vector assembles into virus-like particles which are secreted into the cell culture medium (Gheysen et. al., 1988. *Modern Approaches to New Vaccines*, Cold Spring Harbor Laboratory, N.Y. September 14–18, abstract no. 72).

SUMMARY OF THE INVENTION

This invention pertains to recombinant viral vectors capable of expressing at least two different polypeptides of a heterologous virus capable of self-assembly, in vivo or in vitro, into defective, non-self propagating viral particles, and to methods of producing the recombinant virus. This invention also pertains to intermediate DNA vectors which recombine with a parent virus in vivo or in vitro to produce the recombinant viral vector, and to methods of vaccinating a host with the recombinant viral vector to elicit protective immunity against the correlate heterologous pathogenic virus. In addition, this invention pertains to defective, non-self propagating viral particles, such as HIV, SIV, or picornaviral particles, produced by the recombinant viral vectors; these viral particles may be isolated and used themselves as immunogens for vaccination against pathogenic viruses, or for therapeutic purposes, such as enhancing immune responses in an infected individual, or for targeted delivery of therapeutic agents, such as cytotoxic drugs, to specific cell types.

DETAILED DESCRIPTION OF THE INVENTION

1. Genes Encoding Viral Antigens

Genes encoding viral polypeptides capable of self assembly into defective, non-self propagating viral particles can be obtained from the genomic DNA of a DNA virus or the genomic cDNA of an RNA virus or from available subgenomic clones containing the genes. These genes will include those encoding viral capsid proteins (i.e., proteins that comprise the viral protein shell) and, in the case of enveloped viruses, such as retroviruses, the genes encoding viral envelope glycoproteins. Additional viral genes may also be required for capsid protein maturation and particle self-assembly. These may encode viral proteases responsible for processing of capsid protein or envelope glycoproteins.

As an example, the genomic structure of picornaviruses has been well characterized, and the patterns of protein synthesis leading to virion assembly are clear (Rueckert, R. in *Virology* (1985), B. N. Fields et al., eds. Raven Press, New York, pp 705–738). In picornaviruses, the viral capsid proteins are encoded by an RNA genome containing a single long reading frame, and are synthesized as part of a polyprotein which is processed to yield the mature capsid proteins by a combination of cellular and viral proteases. Thus, the picornavirus genes required for capsid self-assembly include both the capsid structural genes and the viral proteases required for their maturation.

Figure 1:
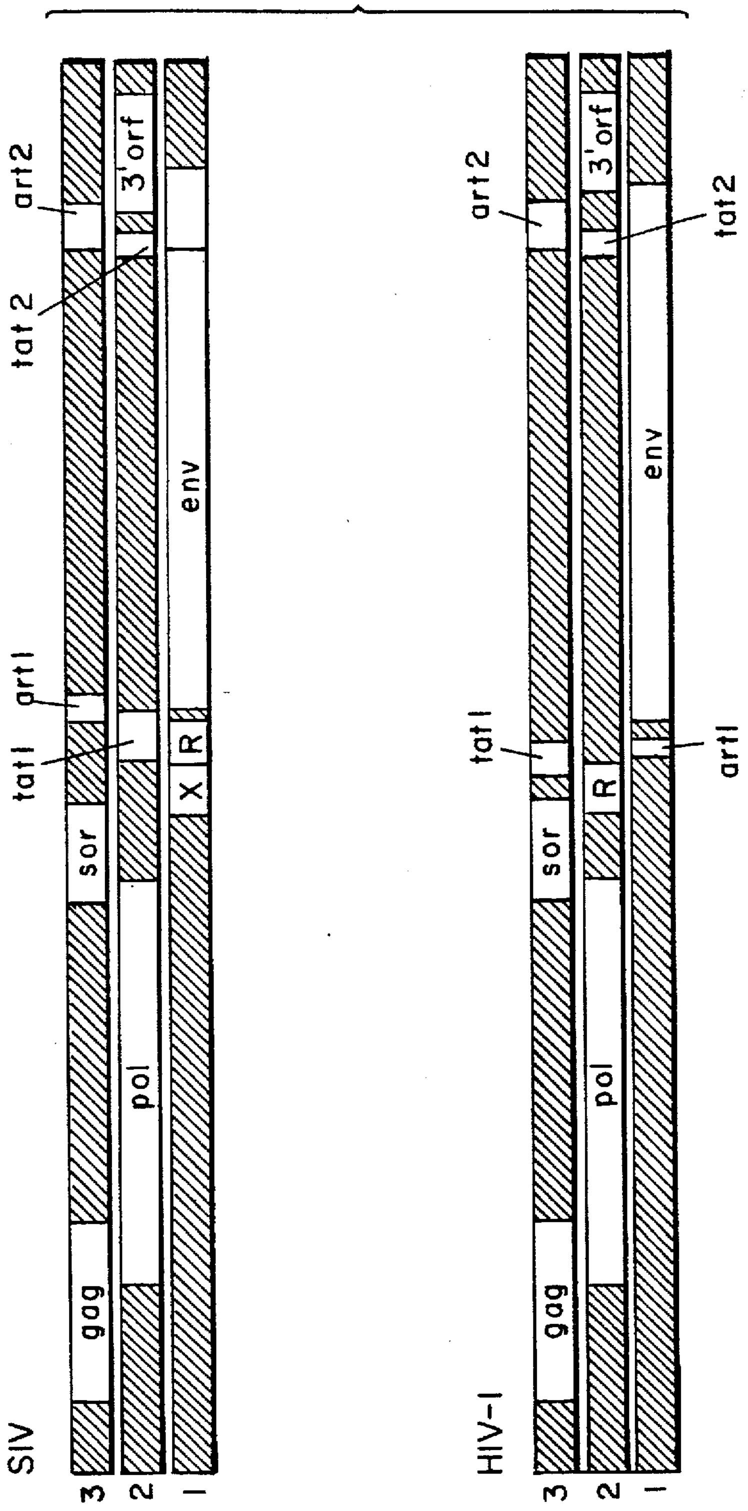
FIG. 1 shows the similar genomic organization of Simian Immunodeficiency Virus (SIV) and Human Immunodeficiency Virus (HIV).

Another example of viruses from which genes encoding self-assembling capsid proteins can be isolated are the retroviruses HIV and SIV. The genomic structures of these viruses have been well characterized, and are represented diagrammatically in FIG. 1. The gene organization of the two viruses is remarkably similar, and homologs of each of the HIV structural genes are present in SIV.

The HIV and SIV gag genes encode the capsid proteins. Like the picornaviral capsid proteins, the HIV and SIV gag proteins are synthesized as a precursor polypeptide that is subsequently processed, by a viral protease, into the mature capsid polypeptides. However, the gag precursor polypeptide can self-assemble into virus-like particles in the absence of protein processing (Gheysen et al., 1988. *Modern Approaches to New Vaccines*, Cold Spring Harbor Laboratory, N.Y. September 14–18, abstract no. 72). Unlike picornavirus capsids, HIV and SIV capsids are surrounded by a loose membranous envelope that contains the viral glycoproteins. These are encoded by the viral env gene.

The examples illustrate the use of SIV and HIV genes selected for expression in recombinant viruses of this invention. These genes and their protein products are outlined in Table 1. The three major virion components derived from the env, gag, and pol genes are synthesized as precursor polyproteins which are subsequently cleaved to yield mature polypeptides as outlined in Table 1.

TABLE 1

SIV and HIV Genes for Recombination into Pox Virus

| Gene | Gene Product[a] | Processed Peptides | |
|---|---|---|---|
| env | gp160 | gp120 | extracellular membrane protein |
| | | gp41 | transmembrane protein |
| gag | p55 | p24 | |
| | | p17 | capsid proteins |
| | | p15 | |
| pol | p160[b] | p10 | protease |
| | | p66/p51 | reverse transcriptase |
| | | p31 | endonuclease |

[a]Sizes given are for HIV proteins; size of the SIV polypeptides may be slightly different.
[b]Part of the gag-pol product.

2. Parent Viruses

A number of viruses, including retroviruses, adenoviruses, herpesviruses, and pox viruses, have been developed as live viral vectors for the expression of heterologous antigens (Cepko et al., 1984. *cell* 37:1053–1062; Morin et al., 1987. *Proc. Natl. Acad. Sci. USA* 84:4626–4630; Lowe et al., 1987. *Proc. Natl. Acad. Sci. USA* 84:3896–3900; Panicali & Paoletti, 1982. *Proc. Natl. Acad. Sci. USA* 79: 4927–4931; Mackett et al., 1982. *Proc. Natl. Acad. Sci. USA* 79:7415–7419). The examples given illustrate the use of the pox virus family. The preferred pox virus is vaccinia virus, a relatively benign virus which has been used for years as a vaccine against smallpox. Vaccinia virus has been developed as an infectious eukaryotic cloning vector (Paoletti and Panicali, U.S. Pat. No. 4,603,112) and recombinant vaccinia virus has been used successfully as a vaccine in several experimental systems. The virus is considered nononcogenic, has a well-characterized genome, and can carry large amounts of foreign DNA without loss of infectivity (Mackett, M. and G. L. Smith, 1986. *J. Gen. Virol.* 67:2067).

3. DNA Vectors for in Vivo Recombination With a Parent Virus

According to the method of this invention, viral genes that code for polypeptides capable of assembly into viral particles are inserted into the genome of a parent virus in such as manner as to allow them to be expressed by that virus along with the expression of the normal complement of parent virus proteins. This can be accomplished by first constructing a DNA donor vector for in vivo recombination with a parent virus.

In general, the DNA donor vector contains the following elements:

i) a prokaryotic origin of replication, so that the vector may be amplified in a prokaryotic host;

ii) a gene encoding a marker which allows selection of prokaryotic host cells that contain the vector (e.g., a gene encoding antibiotic resistance);

iii) at least two heterologous viral genes (e.g., SIV, HIV, or picornavirus genes), each gene located adjacent to a transcriptional promoter capable of directing the expression of the gene; and iv) DNA sequences homologous to the region of the parent virus genome where the foreign gene(s) will be inserted, flanking the construct of element iii.

Methods for constructing donor plasmids for the introduction of multiple foreign genes into pox virus are described in U.S. patent application Ser. No. 910,501, filed Sep. 23, 1986, entitled "Pseudorabies Vaccine", which corresponds to EPO 0261940 the techniques of which are incorporated herein by reference. In general, all viral DNA fragments for construction of the donor vector, including fragments containing transcriptional promoters and fragments containing sequences homologous to the region of the parent virus genome into which foreign genes are to be inserted can be obtained from genomic DNA or cloned DNA fragments. The donor plasmids can be mono-, di-, or multivalent (i.e., can contain one or more inserted foreign gene sequences).

The donor vector preferably contains an additional gene which encodes a marker which will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., 1988, *J. Virol.* 62:1046; Falkner and Moss., 1988, *J. Virol.* 62:1849; Franke et al., 1985. *Mol. Cell. Biol.* 5:1918), as well as genes, such as the *E. coli* lacZ gene, that permit identification of recombinant viral plaques by calorimetric assay (Panicali et al., 1986. *Gene* 47:193–199).

A method for the selection of recombinant vaccinia viruses relies upon a single vaccinia-encoded function, namely the 29K host-range gene product (Gillard et al. 1986. *Proc. Natl. Acad. Sci. USA.* 83:5573). This method was described in U.S. patent application Ser. No. 205,189, filed Jun. 20, 1988, entitled "Methods of Selecting for Recombinant Pox Viruses", which corresponds to WO 89/12103 the teachings of which are incorporated herein by reference. Briefly, a vaccinia virus that contains a mutation in the 29K gene, which is located in the HindIII K/M regions of the viral genome, is used as the host virus for in vivo recombination. The 29K mutation prevents the growth of this virus on certain host cells, for example, RK13 (rabbit kidney) cells. The donor plasmid for insertion of foreign genes contains vaccinia DNA sequences capable of restoring the mutant gene function; these sequences also direct recombination to the site of the mutant gene in the HindIII M region. Thus, recombinant vaccinia viruses regain the ability to grow in RK13 cells, and can be isolated on this basis from the non-recombinant parental viruses, which are unable to grow on these cells.

A preferred DNA vector for recombination with the preferred vaccinia virus comprises:

a. one or more transcriptional promoters (e.g., the vaccinia 7.5K, 30K, 40K, 11K or BamF promoters or modified versions of these promoters), capable of directing expression of adjacent genes in vaccinia virus, each linked to;

b. one or more structural genes encoding viral antigens of interest, each under the control of a transcriptional promoter;

c. a marker for the selection of recombinant parent virus, which may comprise:

(1) a transcriptional promoter (e.g., the BamF promoter of vaccinia virus) linked to a gene encoding a selectable marker (e.g., the *E. coli* lacZ gene); or (2) parent virus structural gene sequences which restore a viral host-range or other virus growth promoting function (e.g., the 29K polypeptide of vaccinia);

d. DNA sequences homologous with a region of the parent virus flanking the construct of elements a–c (e.g., the vaccinia TK or HindIII M sequences);

e. a vector backbone for replication in a prokaryotic host including a marker for selection of bacterial cells transformed with the plasmid (e.g., a gene encoding antibiotic resistance).

4. Integration of Foreign DNA Sequences into the Viral Genome and Isolation of Recombinants Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (Panicali and Paoletti, U.S. Pat. No. 4,603,112).

Following in vivo recombination, recombinant viral progeny can be identified by one of several techniques. For example, if the DNA donor vector is designed to insert foreign genes into the parent virus thymidine kinase (TK) gene, viruses containing integrated DNA will be $TK^-$ and can be selected on this basis (Mackett et al., 1982, *Proc. Natl. Acad. Sci. USA* 79:7415). Alternatively, co-integration of a gene encoding a marker or indicator gene with the foreign gene(s) of interest, as described above, can be used to identify recombinant progeny. One preferred indicator gene is the *E. coli* lacZ gene: recombinant viruses expressing beta-galactosidase can be selected using a chromogenic substrate for the enzyme (Panicali et al., 1986, *Gene* 47:193). A second preferred indicator gene for use with recombinant vaccinia virus is the vaccinia 29K gene: recombinant viruses that express the wild type 29K gene-encoded function can be selected by growth on RK13 cells.

As described more fully in the Examples, monovalent and divalent donor plasmids containing HIV or SIV genes were recombined into vaccinia at either the TK gene or the HindIII M region and recombinant viruses were selected as described above.

5. Characterizing the Viral Antigens Expressed by Recombinant Viruses

Once a recombinant virus has been identified, a variety of methods can be used to assay the expression of the polypeptide encoded by the inserted gene. These methods include black plaque assay (an in situ enzyme immunoassay performed on viral plaques), Western blot analysis, radioimmunoprecipitation (RIPA), and enzyme immunoassay (EIA). Antibodies to antigens expressed by viral pathogens are either readily available, or may be made according to methods known in the art. For example, for human or simian immunodeficiency viruses, the antibodies can be (a) for parent virus/SIV recombinants, sera from macaque monkeys infected with SIV; and (b) for parent virus/HIV recombinants, either sera from human patients infected with HIV, or commercially available monoclonal antibodies directed against specific HIV polypeptides.

6. Viral Particle Formation.

Expression analysis described in the preceding section can be used to confirm the synthesis of the polypeptides encoded by inserted heterologous viral genes, but does not address the question of whether these polypeptides self-assemble, in vivo or in vitro, into defective viral particles. Two experimental approaches can be used to examine this issue.

The first approach is to visually examine by electron microscopy lysates of cells infected with recombinant viruses that express one or more viral polypeptides. In the experiments reported below, for example, vaccinia recombinants that express gag, env+gag, or env+gag+pol genes of SIV and/or HIV gave rise to the formation of defective retroviral particles; in cells infected with the recombinants that coexpress gag and env polypeptides, the particle envelope contained the envelope glycoproteins as shown by the presence of glycoprotein "spikes" on the surface of the particles. The presence of retroviral envelope glycoproteins on the surface of the particles can be demonstrated with immunogold electron microscopy, using a monoclonal antibody directed against one of the envelope glycoproteins.

In order to further characterize the defective viral particles produced by recombinant viruses expressing viral polypeptides, these particles can be isolated by high speed centrifugation from the culture medium of cells infected with the recombinant viruses in the presence of [$^{35}$S]-methionine. The pellet resulting from centrifugation of the culture medium can be resuspended and both the pellet and the supernatant can be immunoprecipitated with an appropriate antiserum to analyze the viral polypeptides present in each fraction. For example, in the case of recombinants expressing HIV or SIV polypeptides, either human anti-HIV antisera (for vaccinia/HIV recombinants) or macaque anti-SIV antisera (for vaccinia/SIV recombinants) can be used for these analyses.

In the case of recombinant viruses that coexpress HIV or SIV env and gag polypeptides, the pellet will contain both envelope and core proteins if retroviral particles are formed. As described in the examples, when this experiment was performed using vaccinia recombinants that coexpress HIV or SIV env and gag polypeptides, the pellet contained both env and gag polypeptides, as would be expected if these polypeptides were assembling into defective retroviral particles. By contrast, the supernatant contained only the envelope glycoprotein gp120.

To further characterize the material in the pellet resulting from centrifugation of the culture medium, the pellet can be resuspended and analyzed on a sucrose gradient. The gradient can then be fractionated and the fractions immunoprecipitated with the appropriate antiserum. These experiments show whether the pellet contains material banding at the density expected for defective viral particles.

These methods can also be used to determine whether expression of viral polypeptides directed by two different viruses present in the same infected cell gives rise to the production of defective viral particles. For example, these experiments can be performed using cells coinfected in vitro with one recombinant expressing gag and a second recombinant expressing env. The simultaneous expression in a single cell of both env and gag polypeptides, whether directed by a single divalent recombinant virus or by two different monovalent viruses, would be expected to result in the formation of defective retroviral particles that contain a protein core comprising gag polypeptides surrounded by an envelope containing virally-encoded envelope glycoproteins.

7. Vaccines

Live recombinant viral vectors that express heterologous viral antigens capable of self-assembly into defective non-self-propagating virus particles can be used to vaccinate humans or animals susceptible to infection if the viral vector used to express the heterologous defective virus particles infects but does not cause significant disease in the vaccinated host. Examples of such benign viral vectors include certain pox viruses, adenoviruses, and herpes viruses. For example, vaccination with live recombinant vaccinia virus is followed by replication of the virus within the host. During replication, the viral genes are expressed along with the normal complement of recombinant virus genes. Thus, during the two-week post-immunization period when the live recombinant virus is replicating (Fenner, F., in *Virology*, Fields et al., eds. Raven Press, New York, 1985, pp 661–684), viral antigens may be presented to the host immune system in a manner that closely mimics the presentation of antigens in an authentic viral infection, that is, as defective, non-self-propagating viral particles extremely similar to the native virus. Viral antigens repeatedly presented both as free particles and in association with recombinant virus-infected cells may have the potential to prime the immune system to recognize and eliminate the virus during the early events of viral infection.

Alternatively, the defective virus particles produced by these recombinant vector viruses can be isolated from cells infected in vitro with the recombinant vector viruses and from the culture medium of these infected cells, and themselves used for vaccination of individuals susceptible to viral infection. These particles resemble the native virus, but will not contain infectious viral genetic material. Consequently, they offer the advantage of conventional killed virus vaccine preparations: the ability authentically to present immunogenic antigens to the immune system of the vaccinated host. At the same time such particles circumvent the major drawbacks to the use of killed virus as a vaccine for the prevention of infection, including the danger of incomplete inactivation of killed virus preparations and, as for,the case of certain viruses, such as retroviruses, the reluctance to introduce a complete viral genome (the HIV genome, for example) into seronegative individuals.

Vaccine compositions utilizing these defective virus particles would generally comprise an immunizing amount of the viral particles in a pharmaceutically acceptable vehicle. The vaccines would be administered in a manner compatible with the dosage formulation, and in such amount as would be therapeutically effective and immunogenic.

Finally, the purified particles may be used in combination with live recombinant viruses as part of a total vaccination protocol, either as the primary immunizing agent, to be followed by vaccination with live recombinant virus, or to boost the total immune response after primary vaccination with live recombinant virus.

8. Therapeutic Use of Recombinant Viruses Expressing Viral Antigens Capable of Assembling into Defective Viral Particles; Therapeutic Use of Defective Viral Particles Produced by These Recombinant Viruses Even if immunization cannot protect against infection, immunization of a previously infected individual might prolong the latency period of that virus within the individual. This may be particularly important in the case of viral infections characterized by long latency periods, such as HIV infection. The long incubation time between HIV infection and the development of clinical AIDS may be due to an immune response to the initial infection which persists with health and wanes with disease. If this is the case, boosting the immune response by immunization with HIV antigen/parent virus recombinants that produce retroviral-like particles, or alternatively, with the purified particles themselves, may prevent the development of disease and reduce contagiousness (Salk, 1987. *Nature* 327:473).

9. Therapeutic Use of Defective Virus Particles as Agents for Targetted Drug Delivery Defective, non-self-propagating virus particles can also be used to deliver certain drugs (e.g. cytotoxic drugs, antiviral agents) to virus receptor-bearing cells. Such drugs may be coupled, by techniques known in the art, to the outer surface of the virus particle, or incorporated within, and delivered with high specificity to target cells. For example, cytotoxic drugs may be coupled to defective HIV particles and delivered with a high degree of specificity to $CD4^{+}T$ cells, since the HIV envelope glycoprotein present on these particles binds specifically and with high affinity to the CD4 molecule. Similarly, poliovirus particles, for example, preferentially bind cells of the nasopharynx and gut, and thus can be used to direct delivery of specific agents to these cells.

10. Diagnostic Uses of Virus-Like Particles

Immunogenic virus-like particles can be used to diagnose viral infection. The particles can be used to raise a panel of monoclonal antibodies and polyclonal antisera which recognize various epitopes on the virion. These monoclonal and/or polyclonal antibodies can be used individually or together as capture antibodies for an immunoassay to detect the presence of virus in urine, blood, or feces.

Alternately, the particles themselves can be used as antigens for an immunoassay to detect the presence of antibody in urine, blood, or feces. Particularly preferred immunoassays are solid phase immunometric assays (enzymetric radiometric). In such assays, the virus-like particle is immobilized on a solid phase to provide an immunoadsorbent. The techniques for use of solid phase immunoadsorbents are known in the art.

This invention is illustrated further by the following examples:

EXAMPLES

Materials and Methods

Cells and Virus

*E. coli* strain MC1061 (Casadaban and Cohen, 1980, *J. Mol. Biol.* 138:179) was used as the host for the growth of all plasmids. The monkey kidney cell line BSC-40 (Brockman & Nathans, 1974. *Proc. Natl. Acad. Sci. USA* 71:942), the thymidine kinase-deficient (TK–) human cell line Hu143TK– (Bacchetti and Graham, 1977. *Proc. Natl. Acad. Sci. USA* 74: 1590) and the rabbit kidney cell line RK13 (ATCC #CCL37; Beale et al., 1963, *Lancet* 2:640) were used for vaccinia infections and transfections.

Vaccinia virus strain NYCBH (ATCC #VR-325) and 29K– lacZ+ strain vABT33 (see U.S. patent application Ser. No. 205,189, filed Jun. 10, 1988, which corresponds to WO89/12108 the teachings of which are incorporated herein by reference) were used as the parental viruses for in vivo recombination.

Enzymes

Restriction enzymes were obtained from New England BioLabs or Boehringer-Mannheim. The large fragment of DNA polymerase (Klenow) was obtained from United States Biochemical Corp., T4 DNA polymerase was obtained from New England BioLabs, and T4 DNA ligase was obtained from Boehringer-Mannheim.

Molecular Cloning Procedures

Restriction enzyme digestions, purification of DNA fragments and plasmids, treatment of DNA with Klenow, T4 DNA polymerase, ligase, or linkers and transformation of E. coli were performed essentially as described (Maniatis et al., *Molecular Cloning: A Laboratory Manual*, Cold Spring Harbor Laboratory, Cold Spring Harbor, N.Y., 1982, incorporated herein by reference).

Oligonucleotide mutagenesis was performed using synthetic oligonucleotides obtained from the Biology Department, Brandeis University, with reagents supplied by Amersham and used according to the manufacturer's instructions.

Preparation of Vaccinia Virus Recombinants

Viral infection, transfections, plague purification and virus amplification were performed essentially as described (Spyropoulos et al., 1988, *J. Virol.* 62:1046). 29K+ recombinants were selected and purified on RK13 cells (see U.S. patent application Ser. No. 205,189, filed Jun. 10, 1988which corresponds to WO89/12103, the teachings of which are incorporated by reference herein). $TK^{-}$ recombinants were selected and purified in the presence of 50 uM bromodeoxyuridine.

Vaccinia Virus Genomic Analysis

DNA was extracted from vaccinia virus-infected cells as described (Esposito et al., 1981, *J. Virol. Methods* 2:175) and analyzed by restriction enzyme digestions and Southern hybridization as described (Maniatis et al., *Molecular Cloning: A Laboratory Manual*, Cold Spring Harbor Laboratory, Cold Spring Harbor, N.Y., 1982).

Protein Analysis

Black plaque assay and immunoprecipitation analysis were performed essentially as described in (Smith et al., 1983. *Proc. Natl. Acad. Sci. USA* 80:7155 and Wittek et al., 1984. *J. Virol* 49:371); See also, U.S. patent application Ser. No. 910,501 filed Sep. 23, 1986 which corresponds to EP0261940 incorporated by reference herein. For black plaque and immunoprecipitation assays, macaque polyclonal antiserum against whole SIV, or human antiserum against whole HIV, were used. For immunoprecipitation analysis, vaccinia-infected cells were labelled either with $[^3H]$-glucosamine or $[^{35}S]$-methionine.

Biochemical Analysis of Recombinant Vaccinia-directed Retroviral Particle Formation BSC-40 cells infected with the wild type or recombinant vaccinia virus were labeled with $[^{35}S]$-methionine, using the same labeling procedure used for immunoprecipitation analysis. After 16–18 hours, the medium from infected cells was collected and clarified by centrifugation at 1000 rpm for 5 minutes. The resulting supernatant was centrifuged at 24K for 90 minutes in an SW28 rotor. The supernatant was removed, and the resulting pellet was resuspended in 3 ml PBS buffer (136 mM NaCl, 2.7 mM KCl, 8.1 mM $Na_2HP0_4$, 1.5 mM $KH_2PO_4$). Samples from the supernatant and pellet were subjected to immunoprecipitation analysis, using macaque anti-SIV antiserum, or human anti-HIV antiserum as described in the preceding section.

Analysis of Recombinant Vaccinia-directed Retroviral Particle Formation by Electron Microscopy BSC-40 cells were infected with wild type or recombinant vaccinia virus at a multiplicity of 10 for 16–18 hours as described above. Medium was then removed, and infected cells were washed twice in 0.2% gelatin in PBS buffer.

For immunogold staining, samples were preincubated in 10% goat serum in PBS/gelatin for 30 minutes at 4° C., then incubated in the appropriate monoclonal antibody diluted in PBS/gelatin for 60 minutes. Samples were then washed in PBS/gelatin twice and incubated with a 1:20 dilution of goat anti-mouse IgG conjugated with gold (5nm) in PBS with 1% fetal calf serum, 0.1% sodium azide, and 5% human antibody serum for 60 minutes. Cells were again washed in PBS/gelatin.

Untreated or immunogold stained cells were fixed in 0.25% glutaraldehyde in 0.1M sodium cacodylate buffer (pH 7.2) overnight, then washed in 0.1M sodium cacodylate buffer (pH 7.2) twice. Samples were then fixed in 1% $OsO_4$/0.1M cacodylate buffer (pH 7.2) for 1½ hours and then washed twice in 0.1M cacodylate buffer (pH 7.2). Samples were then dehydrated in the following graded alcohols for 10 minutes each: 50, 70, 80, 95, 100 (3X). Samples were then treated with propylene oxide twice for five minutes each, then overnight in uncapped vials in propylene oxide (4 parts)/epox812 (6 parts). Samples were then embedded in epox812 and cured for 36 hours.

Sections were cut on Sorval porter Blum MT-2 ultramicrotome at 1000 A, stained with alcoholic uranyl acetate and Sato's lead stain (Sato, T. 1968. *J. Elect. Mic.* (*Japan*) 17:158–159), and viewed on a JEOL electron microscope.

EXAMPLE 1

Construction of Recombinant Plasmids Containing SIV Genes

Figure 2:
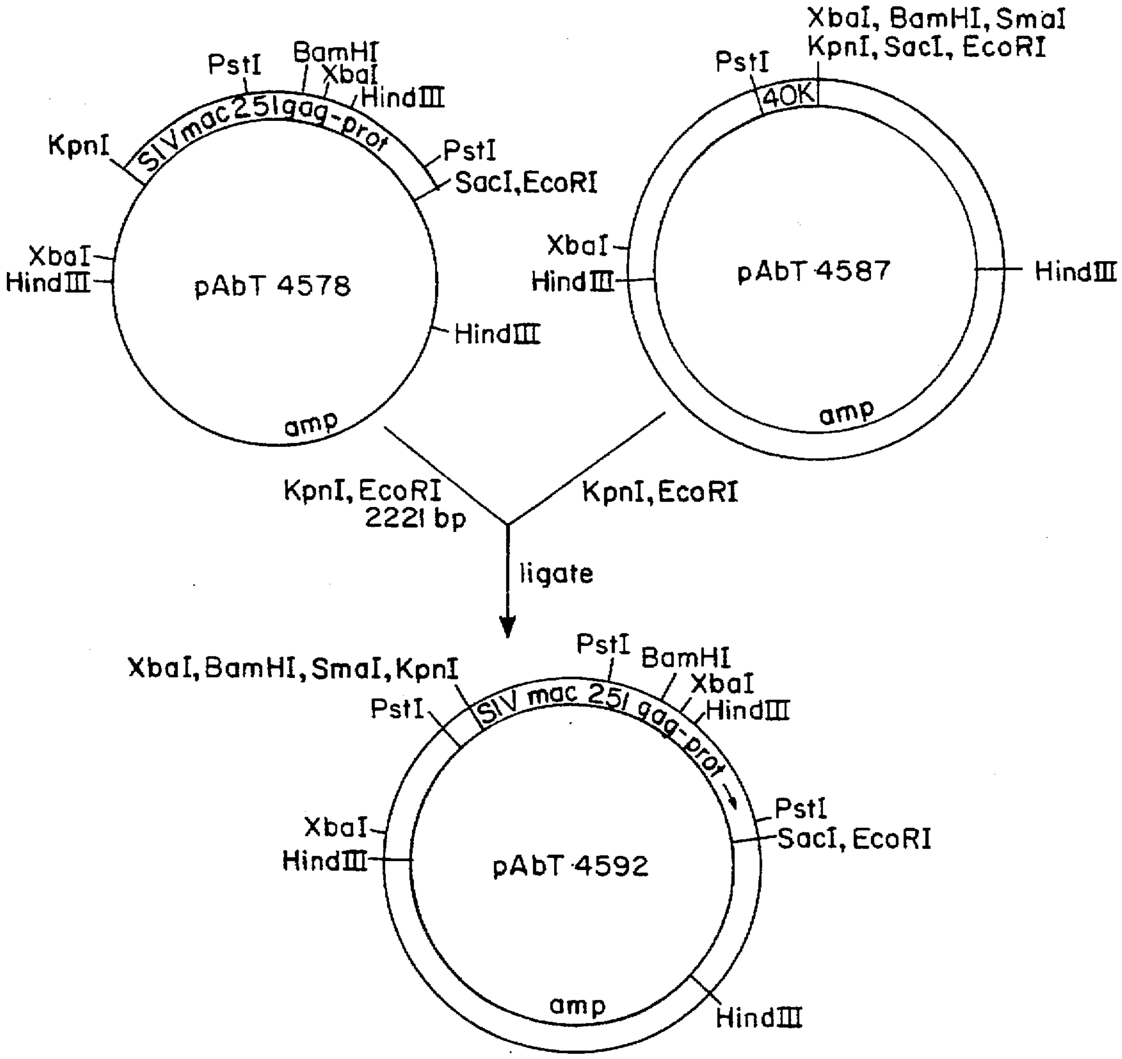
FIG. 2 shows the construction of pAbT4592, a plasmid vector for the insertion and expression of SIVmac251 gag and protease in vaccinia virus. pAbT4592 contains the gag-prot gene under the control of a vaccinia 40K promoter, flanked by vaccinia DNA for directing recombination into the vaccinia HindIII M region. The vector DNA includes the 29K host-range gene for selection of vaccinia recombinants and a bacterial replicon and ampicillin-resistance gene for growth and selection in *E. coli.*
Figure 3:
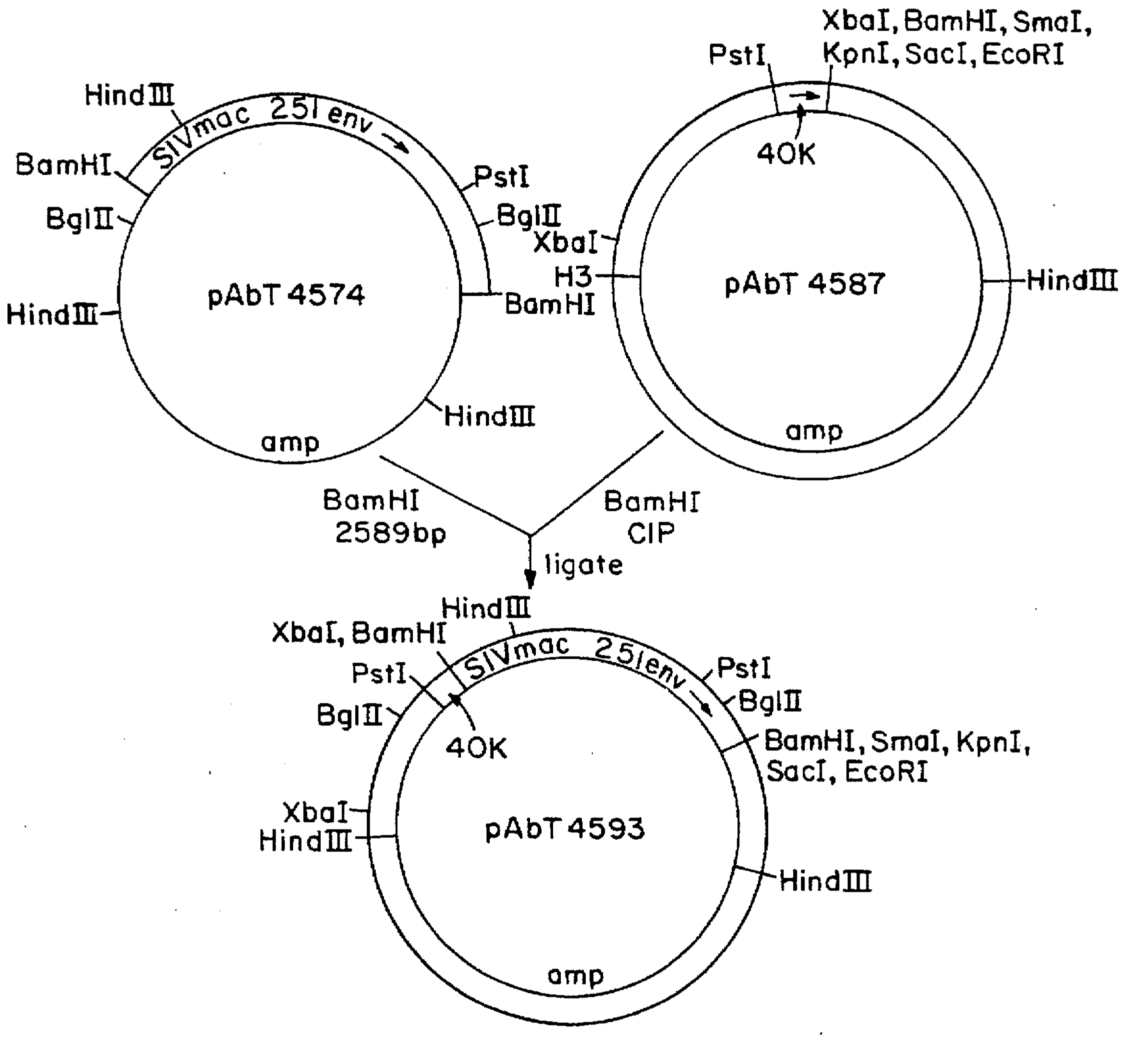
FIG. 3 shows the construction of pAbT4593, a plasmid vector for the insertion and expression of SIVmac251 env in vaccinia virus. pAbT4593 contains the env gene under the control of the vaccinia 40K promoter, flanked by vaccinia DNA for directing recombination into the vaccinia HindIII M region. The vector DNA includes the 29K host-range gene for selection of vaccinia recombinants and a bacterial replicon and ampicillin- resistance gene for growth and selection in *E. coli.*
Figure 4:
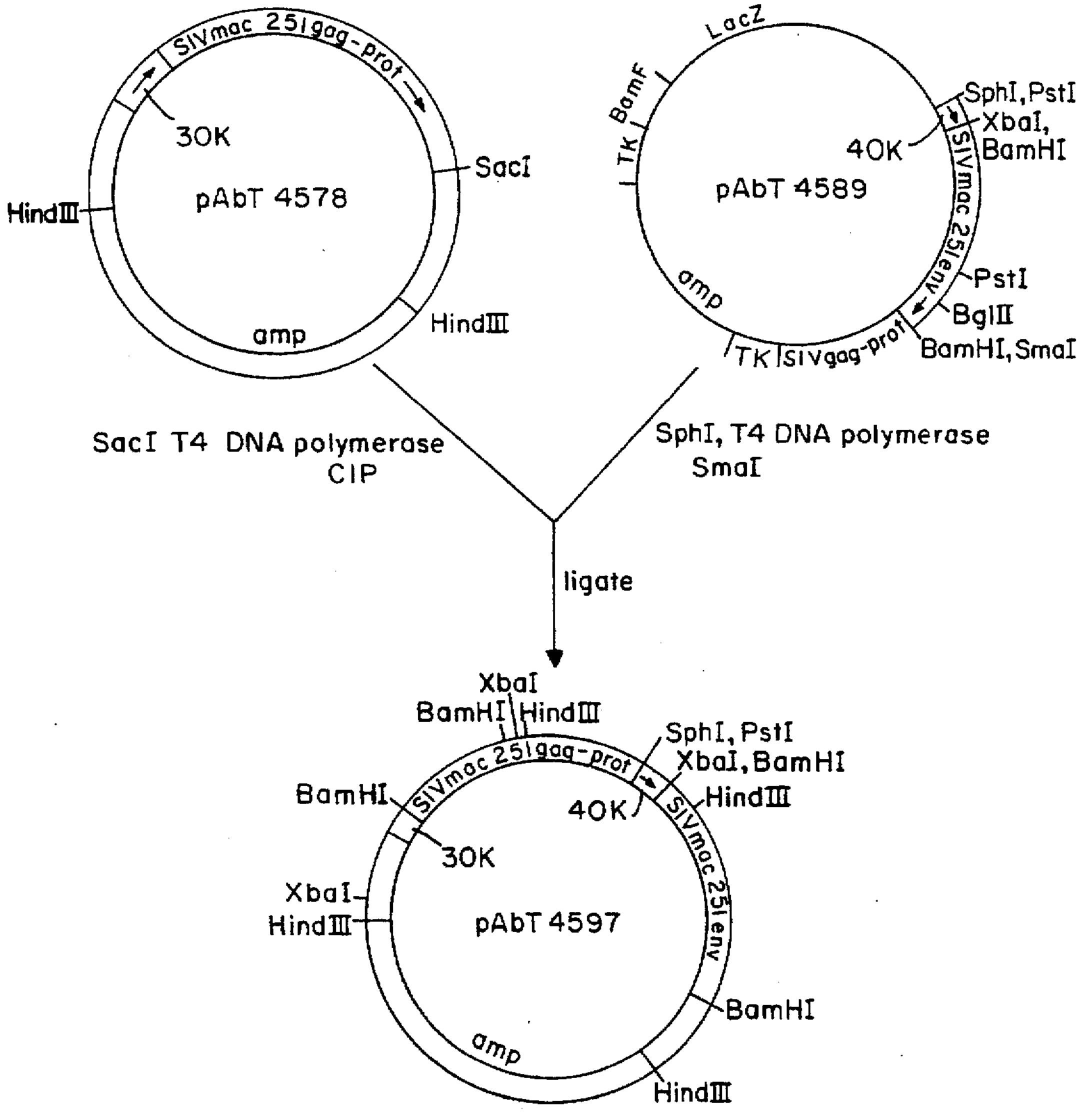
FIG. 4 shows the construction of pAbT4597, a plasmid vector for the insertion and expression of SIVmac251 env and gag-prot in vaccinia virus. pAbT4573 contains the gag-prot gene under the control of the vaccinia 30K promoter and the env gene under the control of the vaccinia 40K promoter. These genes are flanked by vaccinia DNA for directing recombination into the vaccinia HindIII M region. The vector DNA includes the 29K host-range gene for selection of vaccinia recombinants and a bacterial replicon and ampicillin-resistance gene for growth and selection in *E. coli.*

This example illustrates the construction of recombinant plasmids containing SIV genes for in vivo recombination with vaccinia virus (in vivo recombination (IVR) vectors). The construction and structure of plasmids pAbT4532B, pAbT4533, pAbT4536, pAbT4537, pAbT4574, pAbT4578, pAbT4582B, pAbT4583 and pAbT4589 is described in U.S. patent application Ser. No. 205,454, filed Jun. 10, 1988 which corresponds to WO 89/12095. The construction and structure of plasmid pAbT4027 is described in U.S. patent application Ser. No. 910,501, filed Sep. 23, 1986 which corresponds to EP 0261940. The construction and structure of plasmid pAbT4587 is described in U.S. patent application Ser. No. 229,343, filed Aug. 5, 1988 which corresponds to WO90/01546. The teachings of the above- mentioned patent applications are incorporated by reference herein.

pAbT4592 (FIG. 2): pAbT4578 (See U.S. patent application Ser. No.205,454, filed Jun. 10, 1988 which corresponds to WO 90/01546) was digested with KpnI and EcoRI, and a 2221 base pair (bp) fragment was isolated. This fragment was ligated to pAbT4587, which had been digested with KpnI and EcoRI, to give the plasmid pAbT4592. pAbT4592 is a vector for the insertion and expression of SIVmac251 gag and protease in vaccinia virus. pAbT4592 contains the gag-prot gene under the control of the vaccinia 40K promoter, flanked by vaccinia HindIII M region. The vector DNA includes the 29K host-range gene for selection of vaccinia recombinants and a bacterial replicon and ampicillin-resistance gene for growth and selection in *E. coli.* pAbT4593 (FIG. 3): pAbT4574 (U.S. patent application Ser. No.205,454) was digested with BamHI, and a 2589 bp fragment was isolated. This fragment was ligated to pAbT4587, which had been digested with BamHI and treated with calf alkaline phosphatase (CIP), to give the plasmid pAbT4593. pAbT4593 is a vector for the insertion and expression of SIVmac251 env in vaccinia virus. pAbT4593 contains the env gene under the control of the vaccinia 40K promoter, flanked by vaccinia DNA for directing recombination into the vaccinia HindIII M region. The vector DNA includes the 29K host-range gene for selection of vaccinia recombinants and a bacterial replicon and ampicillin-resistance gene for growth and selection in *E. coli.* pAbT4597 (FIG. 4): pAbT4578 (U.S. patent application Ser. No.205,454 which corresponds to WO89/12095) was digested with SacI, and the digested DNA was treated first with T4 DNA polymerase, and then with CIP. pAbT4589 was digested with SphI, then treated with T4 DNA polymerase, and finally digested with SmaI. A 2750 bp fragment was isolated from the digested pAbT4589; this fragment was ligated to the SacI digested pAbT4578 to yield pAbT4597. pAbT4597 is a vector for the insertion and expression of SIVmac251 env and gag-prot in vaccinia virus. pAbT4573 contains the gag-prot gene under the control of the vaccinia 30K promoter and the env gene under the control of the vaccinia 40K promoter. These genes are flanked by vaccinia DNA for directing recombination into the vaccinia HindIII M region. The vector DNA includes the 29K host-range gene for selection of vaccinia recombinants and a bacterial replicon and ampicillin-resistance gene for growth and selection in *E. coli.*

EXAMPLE 2

Figure 5:
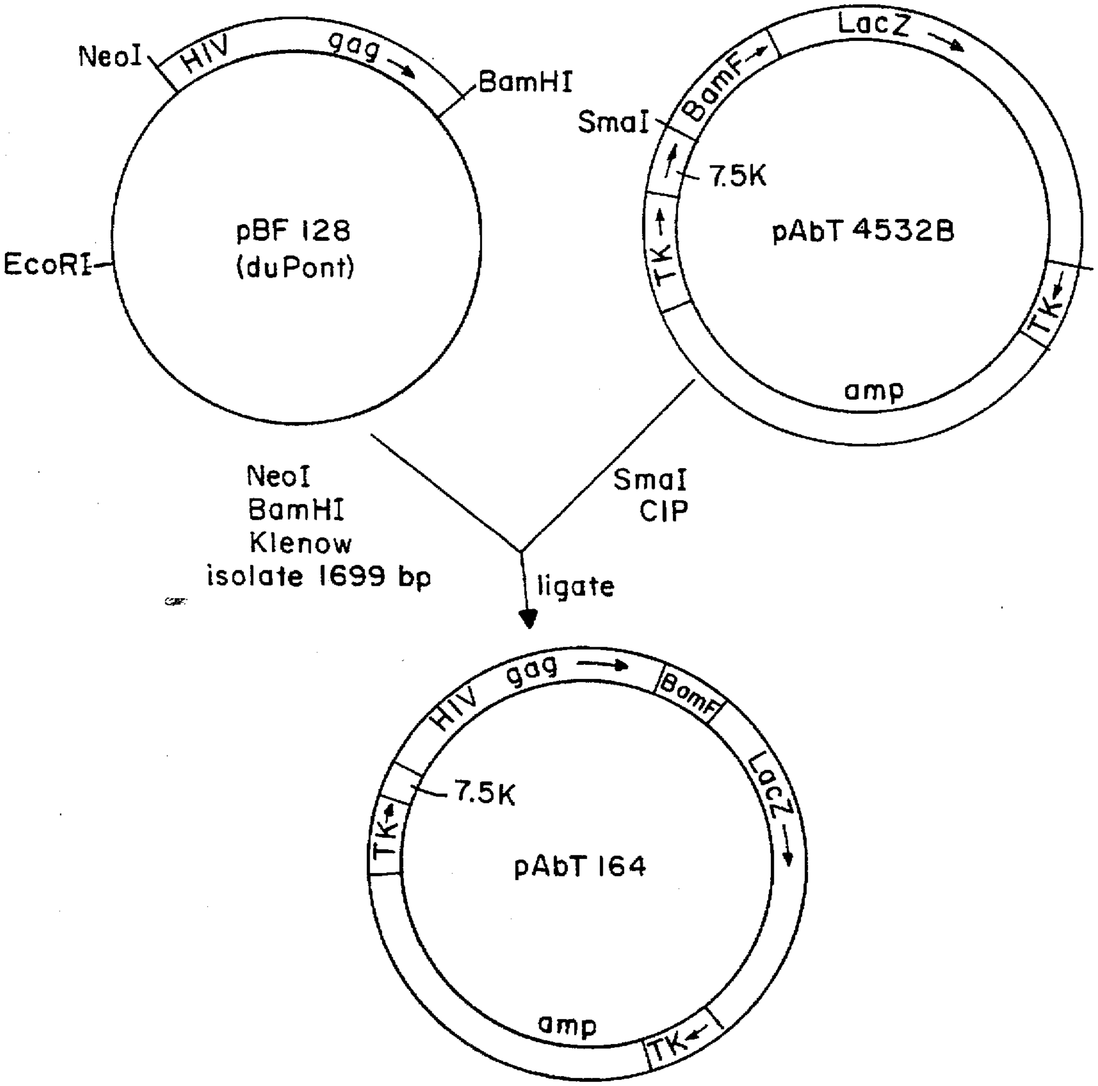
FIG. 5 shows the construction of pAbT164, a plasmid vector for the insertion and expression of HIV-1 gag in vaccinia. pAbT164 contains the HIV gag gene under the control of the vaccinia 7.5K promoter, the DNA regions flanking the vaccinia TK gene for directing recombination in vaccinia, the lacZ gene under the control of the vaccinia BamF promoter for selection of vaccinia recombinants and a bacterial replicon and ampicillin-resistance gene for growth and selection in *E. coli.*
Figure 6A:
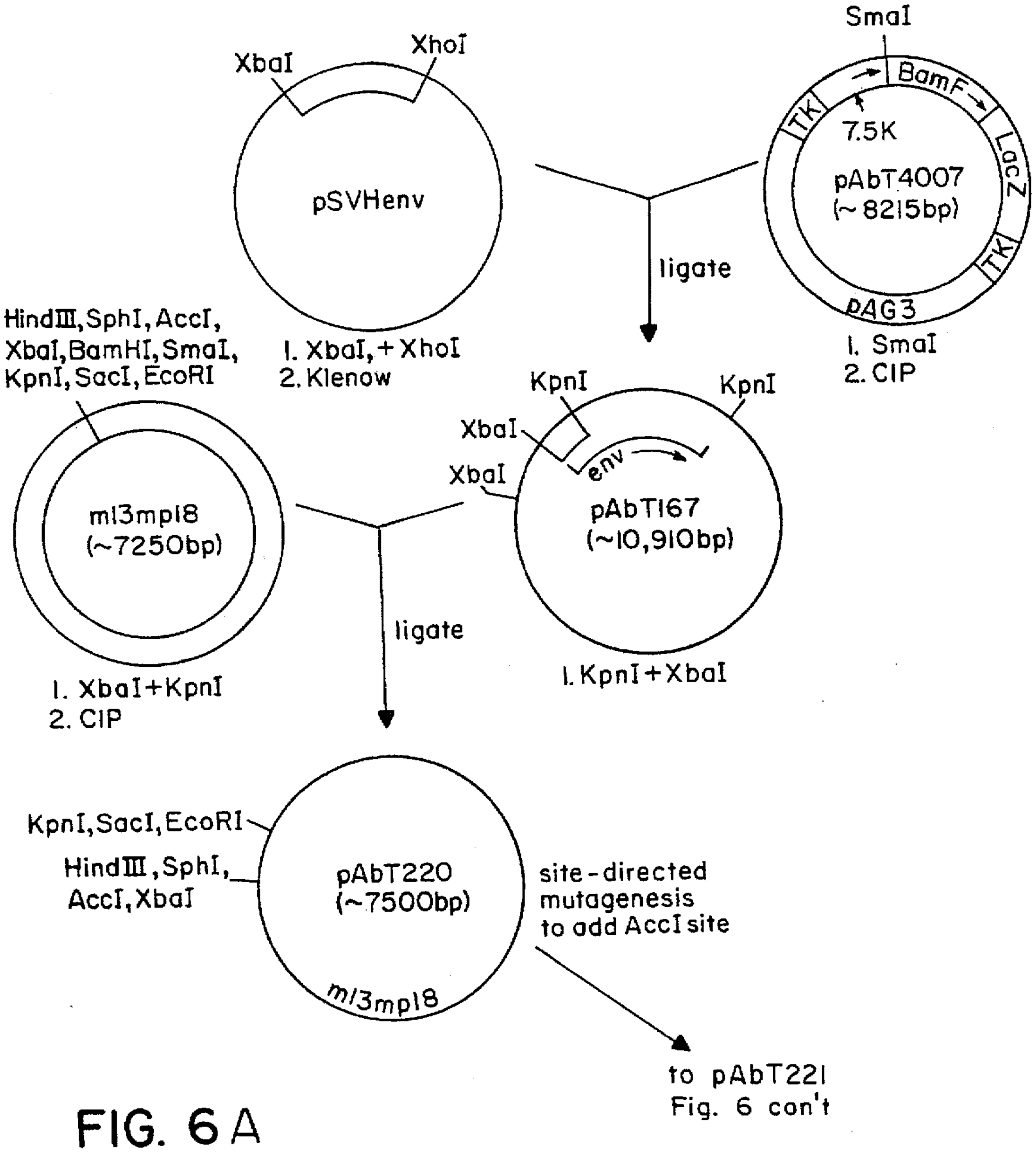
FIG. 6 parts A, B and C shows the construction of pAbT4603, a plasmid vector for the insertion and expression of HIV-1 env gene under the control of the vaccinia 40K promotor, flanked by vaccinia DNA for directing recombination into the vaccinia HindIII M region. The vector DNA includes the 29K host-range gene for selection of vaccinia recombinants and a bacterial replicon and ampicillin resistance gene for growth and selection in *E. coli.*
Figure 6B:
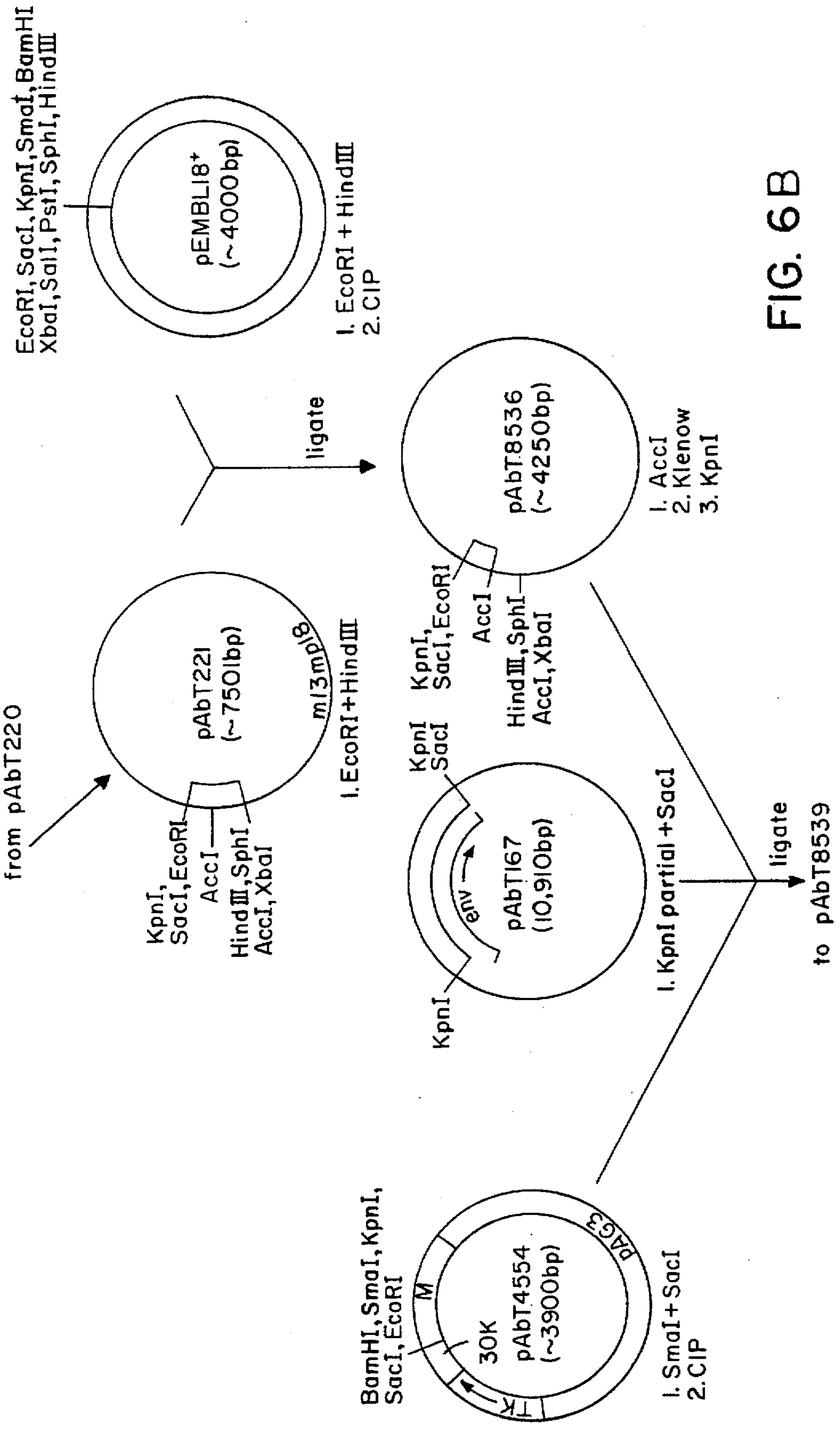
Figure 6C:
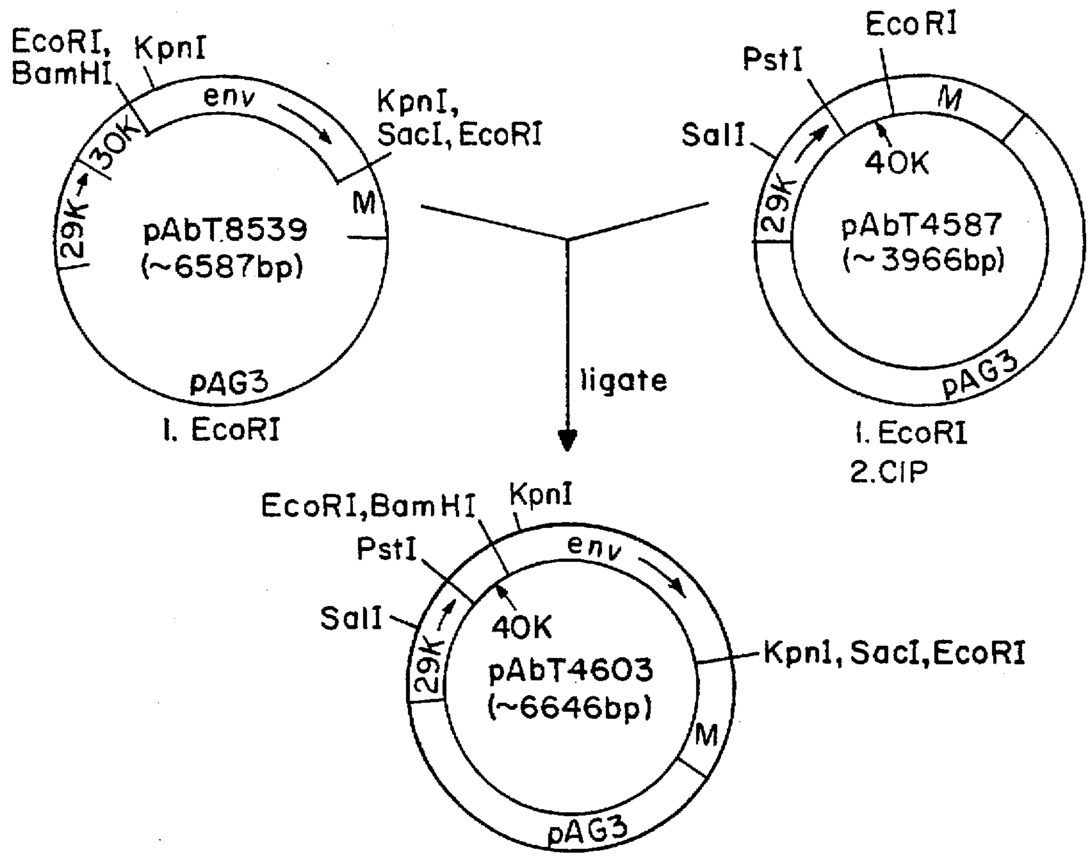

Construction of Recombinant Plasmids Containing HIV Genes pSVHenv and PBF128 are plasmids that contain portions of the HIV-1 strain B10 genome; these were obtained from E.I. Dupont de Nemours and Company. pHXBc2 is a plasmid that contains portions of the HIV-1 strain HSB2 genome, it was obtained from Dr. Joseph Sodroski of the Harvard Medical School. The construction and structure of plasmids pAbT4532B and pAbT4554 were described in U.S. patent application Ser. No. 205,454, filed Jun. 10, 1988 which corresponds to WO89/12089. The construction and structure of plasmid pAbT4007 is described in U.S. patent application Ser. No. 910,501, filed Sep. 23, 1986 which corresponds to EP 0261940. The teachings of the above-mentioned patent applications are incorporated by reference herein.

pAbT164 (FIG. 5) Plasmid pBF128 was digested with NcoI and BamHI and treated with the Klenow fragment of DNA polymerase; a 1700 bp fragment containing the HIV-1 gag gene was isolated from this digest. This fragment was ligated to plasmid pAbT4532B which had been digested with SmaI and treated with CIP, to give the plasmid pAbT164.

pAbT164 is a vector for the insertion and expression of HIV-1 gag in vaccinia. pAbT164 contains the HIV gag gene under the control of the vaccinia 7.5K promoter, the DNA regions flanking the vaccinia TK gene for directing recombination in vaccinia, the lacZ gene under the control of the vaccinia BamF promoter for selection of vaccinia recombinants and a bacterial replicon and ampicillin-resistance gene for growth and selection in *E. coli.* pAbT4603 (FIG. 6)

Plasmid pSVHenv was digested with XbaI and XhoI and treated with the Klenow fragment of DNA polymerase; a 2700 bp fragment containing the HIV-1 env gene was isolated from this digest. This fragment was ligated to plasmid pAbT4007 which had been digested with SmaI and treated with CIP, to give the plasmid pAbT167.

pAbT167 was digested with KpnI and XbaI and a 225 bp fragment containing the 5' end of the HIV-1 env gene was isolated from this digest. This fragment was ligated to m13mp18 bacteriophage DNA (New England BioLabs) which had been digested with XbaI and KpnI and treated with CIP, to create pAbT220. The 5' end of the env gene was modified to remove most of the 5' non-coding sequences by oligonucleotide-directed mutagenesis, as described in Materials and Methods. Using the oligonucleotide 5'-GAAAGAGCAGTAGACAGTGG-3' (Biology Department, Brandeis University), an AccI site was inserted approximately 10 bp upstream from the ATG initiation codon of the env coding sequence, creating pAbT221. pAbT221 was digested with EcoRI and HindIII, and an approximately 230 bp fragment was isolated. This was ligated to the plasmid pEMBL18+ (Dente et al., 1983. *Nucl. Acids Res.* 11:1645) which had been digested with EcoRI and HindIII and treated with CIP, to give the plasmid pAbT8536.

pAbT8536 was digested with AccI, treated with the Klenow fragment of DNA polymerase, and then digested with KpnI. A 138 bp fragment containing the mutagenized 5' non-coding region of the env gene was isolated from this digest. The plasmid pAbT167 was digested with KpnI and SadI, and a 2461 bp fragment containing most of the env gene sequence was isolated. The 138 bp fragment from pAbT8536 and the 2461 bp fragment from pAbT167 were ligated to pAbT4554 which had been digested with SmaI and SacI and treated with CIP, to yield the plasmid pAbT8539.

pAbT8539 was digested with EcoRI and a 2682 bp fragment containing the env gene was isolated. This was ligated to pAbT4587 which had been digested with EcoRI and treated with CIP, to yield the plasmid pAbT4603.

pAbT4603 is a vector for the insertion and expression of HIV-1 env in vaccinia virus. pAbT4603 contains the env gene under the control of the vaccinia 40K promoter, flanked by vaccinia DNA for directing recombination into the vaccinia HindIII M region. The vector DNA includes the 29K host-range gene for selection of vaccinia recombinants and a bacterial replicon and ampicillin-resistance gene for growth and selection in *E. coli.* pAbT621 (FIG. 7)

Figure 7A:
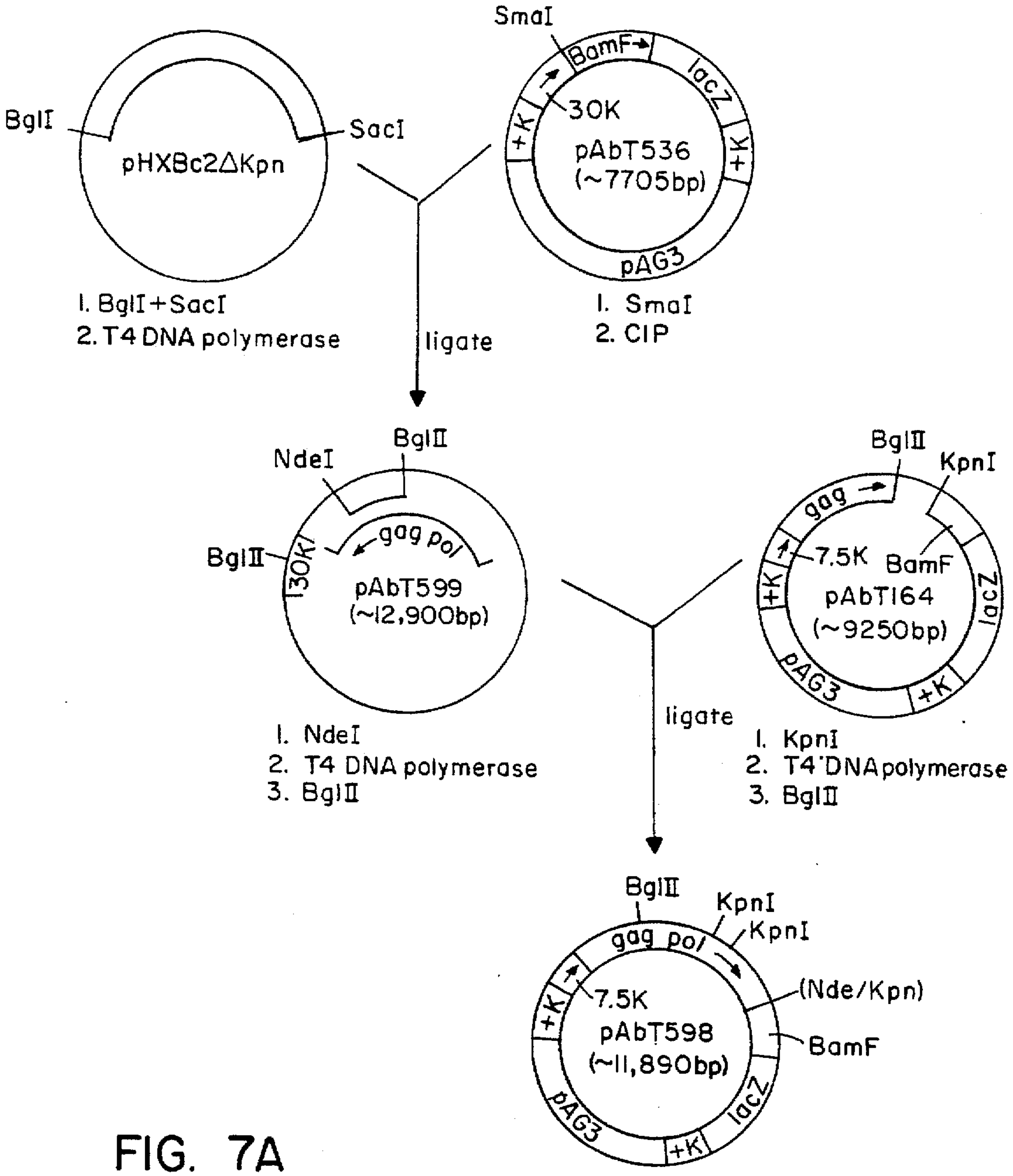
FIG. 7 parts A and B show the construction of pAbT621, a plasmid vector for the insertion and expression of HIV-1 env and gag-prot in vaccinia. pAbT621 contains the HIV env gene under the control of the vaccinia 40K promoter and the HIV gag-prot gene under the control of the vaccinia 30K promoter. These genes are flanked by vaccinia DNA for directing recombination into the vaccinia HindIII M region. The vector DNA includes the 29K host-range gene for selection of vaccinia recombinants and a bacterial replicon and ampicillin-resistance gene for growth and selection in *E. coli.*
Figure 7B:
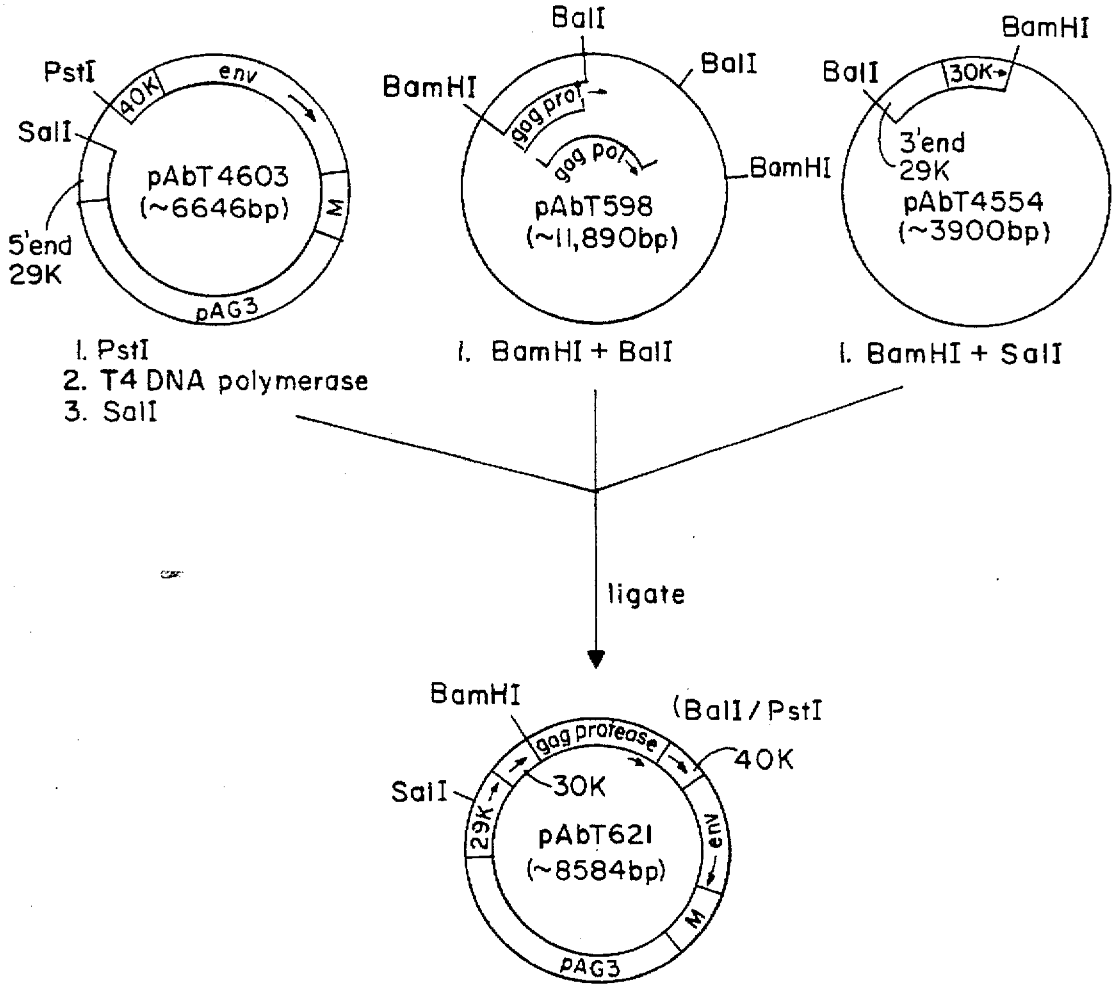

7A. Construction of plasmid pAbT598 (FIG. 7*a*). A plasmid derived from pHXBc2 (Sodroski et al., *Nature* 322:470 (1986)) was digested with BglI and SacI, releasing a fragment corresponding to nucleotide positions 715–6002. This DNA was then treated with T4 DNA polymerase. The 5287 bp fragment containing the HIV-1 gag and pol genes was isolated from this digest and ligated to pAbT4536 which had been digested with SmaI and treated with CIP, to yield the plasmid pAbT599.

pAbT599 was digested with NdeI, treated with T4 DNA polymerase, then further digested with BglII, and a 3027 bp fragment was isolated from this digest. This fragment was ligated to an 8864 bp fragment isolated after digestion of pAbT164 with KpnI, treatment with T4 DNA polymerase, and further digestion with BglII, to yield plasmid pAbT598.

B. Construction of pAbT621 (FIG. 7*b*). pAb4603 was digested with PstI, treated with T4 DNA polymerase, and further digested with Sal I, and a 6326 bp fragment resulting from this digestion was isolated. pAbT598 was digested with BamHI and BalI, and a 1838 bp fragment was isolated. pAbT4554 was digested with SalI and BamHI, and a 420 bp fragment was isolated. These three fragments were ligated together to create pAbT621.

pAbT621 is a vector for the insertion and expression of HIV-1 env and gag-prot in vaccinia. pAbT621 contains the HIV env gene under the control of the vaccinia 40K promoter, the SIV gag-prot gene under the control of the vaccinia 30K promoter. These genes are flanked by vaccinia DNA for directing recombination into the vaccinia HindIII M region. The vector DNA includes the 29K host-range gene for selection of vaccinia recombinants and a bacterial replicon and ampicillin-resistance gene for growth and selection in *E.coli.*

EXAMPLE 3

Construction of Recombinant Vaccinia Viruses Containing HIV-1 or SIVmac251 Genes Under the Control of Vaccinia Promoters.

In vivo recombination is a method whereby recombinant vaccinia viruses are created (Nankano et al., 1982. *Proc. Natl. Acad. Sci. USA* 79:1593; Paoletti and Panicali, U.S. Pat. No. 4,603,112). These recombinant viruses are formed by transfecting DNA containing a gene of interest into cells which have been infected by vaccinia virus. A small percent of the progeny virus will contain the gene of interest integrated into a specific site on the vaccinia genome. These recombinant viruses can express genes of foreign origin (Panicali and Paoletti, 1982, *Proc. Natl. Acad. Sci. USA* 79:4927; Panicali et al., 1983. *Proc. Nati. Acad. Sci. USA* 80:5364).

To insert SIVmac251 or HIV-1 genes into the vaccinia virus genome at the HindIII M region, a selection scheme based upon the 29K host-range gene, which is located in this region (Gillard et al., 1986. *Proc. Natl. Acad. Sci. USA*

83:5573) was used. Recombinant vaccinia virus vAbT33 contains the lacZ gene in place of a portion of the 29K gene. This lacZ insertion destroys the function of the 29K gene; therefore, vAbT33 can not grow on RK13 cells, which require the 29K gene product. Furthermore, vAbT33 forms blue plaques on permissive cells in the presence of the chromogenic substrate for betagalactosidase, Bluogal, due to the presence of the lacZ gene. See U.S. patent application Ser. No. 205,189, filed Jun. 10, 1988 which corresponds to WO 89/12103.

IVR vectors pAbT4592, pAbT4593, pAbT4597, pAbT4603, and pAbT621 were transfected into BSC-40 cells which had been infected with vaccinia virus vAbT33 (see Materials and Methods). Recombinant viruses were selected as white plaques in the presence of Bluogal on RK13 cells. Plaques were picked and purified, and were shown, by Southern analysis, to contain the appropriate SIVmac251 or HIV-1 gene(s): vAbT252 contains SIV gag-prot; vAbT271 contains HIV-1 env; vAbT253 contains SIV env; vAbT264 contains both SIV env and SIV gag-prot; and vAbT344 contains HIV-1 env and gag-prot.

To insert SIVmac251 or HIV-1 genes into the vaccinia virus genome at the TK locus, which is located in the HindIII J region, a selection scheme based on the sensitivity of the $TK^+$ viruses to bromodeoxyuridine (BUdR) was used. Bromodeoxyuridine is lethal for $TK^+$ virus but allows recombinant, $TK^-$ virus to grow. Plasmids for in vivo recombination are therefore transfected into Hu143$TK^-$ cells which have been infected with a $TK^+$ vaccinia virus (see Materials and Methods).

In addition, plasmid vectors for insertion at TK contain the *E. coli* lacZ gene under the control of the vaccinia BamF promoter; recombinant viruses that contain the desired foreign gene(s) also contain the lacZ gene and therefore produce blue plaques when propagated in the presence of the chromogenic substrate for beta-galactosidase, Bluogal. Thus, recombinant viruses are selected in BUDR and are further identifiable as blue plaques in the presence of Bluogal.

To construct a recombinant vaccinia virus that contains the HIV-1 gag gene inserted at the TK locus, the wild type NYCBH virus was used as the parental virus for in vivo recombination with vector pAbT164, to produce the recombinant virus vAbT141.

To construct a recombinant vaccinia virus that contains the SIVmac251 env, gag-prot, and pol genes, vAbT264 was used as the parental virus for in vivo recombination with pAbT4583, an IVR vector that contains the SIVmac251 pol gene under the control of the vaccinia 40K promoter, flanked by DNA homologous to the vaccinia TK gene. This vector is described in U.S. patent application Ser. No. 205,454, filed Jun. 10, 1988 which corresponds to WO 89/12095. This yielded the recombinant virus vAbT277, which contains the SIVmac251 pol gene inserted at the TK locus under the control of the vaccinia 40K promoter, and the SIVmac251 env and gag-prot genes, under the control of the 40K and 30K vaccinia promoters, respectively, inserted at the HindIII M locus.

EXAMPLE 4

Black Plaque Assay for Expression of SIV or HIV-1 Antigens in Recombinant Vaccinia Virus.

The black plaque assay, described in Materials and Methods, is an in situ enzyme-based immunoassay which can detect protein expressed by vaccinia-infected cells. This assay was performed on vaccinia recombinants vAbT252, vAbT253, vAbT264, and vAbT277 using serum from SIV-infected macaques, obtained from Ronald C. Desrosiers (New England Regional Primate Research Center, Southborough, Mass.), and on vAbT141 and vAbT344 using serum from HIV-1 infected human patients, obtained from John Sullivan (University of Massachusetts Medical School, Worcester, Mass.).

Plaques formed by the negative control viruses NYCBH or vAbT33 showed only a background color which was consistent with the background on the cell monolayer itself. Plaques formed by vaccinia recombinants vAbT252, vAbT253, vAbT264, vAbT277, vAbT141, vAbT271 and vAbT344 stained a distinct dark purple color which was much darker than the background on the cell monolayer, showing that these recombinants strongly express SIVmac251 or HIV-1 antigens.

EXAMPLE 5

Immunoprecipitation of SIVmac251 or HIV-1 Antigens from Recombinant Vaccinia Viruses.

Immunoprecipitation analysis was performed on cells infected with recombinant vaccinia viruses vAbT252, vAbT253, vAbT223, vAbT264, vAbT277, vAbT141, vAbT271 and vAbT344 as described in Materials and Methods. The results, which are summarized in Table 1, show that each of these vaccinia recombinants expresses the encoded polypeptide(s).

TABLE 1

Immunoprecipitation of SIVmac251 or HIV-1 polypeptides from recombinant vaccinia viruses

| Vaccinia recombinant | Inserted genes | Proteins observed |
|---|---|---|
| vAbT252 | SIV gag-prot | p55, p40, p24, p15 |
| vAbT253 | SIV env | gp160, gp120, gp32 |
| vAbT264 | SIV env, gag-prot | gp160, gp120, gp32<br>p55, p40, p24, p15 |
| vAbT277 | SIV env, gag-prot, pol | gp160, gp120, gp32<br>p55, p40, p24, p15<br>p64, p53, p10 |
| vAbT141 | HIV gag | p55 |
| vAbT271 | HIV env | gp160, gp120, gp41 |
| vAbT344 | HIV env, gag-prot | gp160, gp120, gp41<br>p55, p40, p24, p17 |

EXAMPLE 6

Biochemical Detection of Retroviral Particles Produced by Vaccinia Recombinants that Express SIV or HIV Antigens.

Expression analysis described in Example 5 can be used to confirm the synthesis of the polypeptides encoded by inserted HIV or SIV genes, but does not address the question of whether these polypeptides self-assemble in vivo into defective viral particles. As one means of determining whether vaccinia recombinants that express env, gag-prot or both env and gag-prot produce retroviral-like particles released into the medium of infected cells, the medium was examined for the presence of structures containing env and/or gag polypeptides which could be pelleted by centrifugation. BSC-40 cells were infected with SIV/vaccinia recombinants vAbT253 (env), vAbT252 (gag-prot) or vAbT264 (env and gag-prot) or with HIV/vaccinia recombinants vAbT141 (gag), vAbT271 (env) or vAbT344 (env and gag-prot). Infected cells were labeled with $[^{35}S]$ methionine as described in Materials and Methods. After 16–18 hours of infection, the medium was collected and clarified by centrifugation at 1000 rpm for 5 minutes. The resulting supernatant was removed and subjected to centrifugation at 24K for 90 minutes in an 8W28 rotor. The supernatant was then removed and the resulting pellet was resuspended in 1 ml PBS buffer (13 mM NaCl, 2.7 mM KCl, 8.1 mM $Na_2HPO_4$, 1.5 mM $KH_2PO_4$). Samples from the supernatant and pellet were subjected to immunoprecipitation analysis, using macaque anti-SIV antiserum, for SIV/vaccinia recombinants, or human anti-HIV antiserum, for HIV/vaccinia recombinants, as described in Materials and Methods. The results showed that for env and gag-prot recombinants vAbT264 and vAbT344, while the supernatant contained only gp120, which had been presumably shed into the culture medium during growth of the SIV/vaccinia recombinant (Kieny et al., 1986. *Bio/Technology* 4:790), the pellet contained not only gp120, but also the env gene-encoded gp32 (for vAbT264) or gp41 (for vAbT344) as well as the gag gene-encoded p55, p40, p24, and p15. These results strongly suggested that the recombinant vaccinia-produced env and gag proteins self-assemble into particles or complexes.

For vAbT141 and vAbT252, which express only the HIV gag or SIV gag-prot proteins, respectively, pelleted material contained gag proteins, consistent with the formation of immature viral particles by self-assembly of gag polypeptides. By contrast, for vAbT253 and vAbT271 which express only the SIV or HIV env glycoproteins, respectively, no immunoprecipitable polypeptides were found in the pellet, although substantial amounts of gp120 were found in the supernatant. These results were consistent with the prediction that defective viral particle formation occurs only when the gag polypeptides are expressed, alone or in combination with other viral structural proteins such as the env glycoproteins.

EXAMPLE 7

Demonstration of Retroviral Particle Formation by Recombinant Vaccinia Viruses that Express SIV or HIV-1 Polypeptides using Electron Microscopy As an additional confirmation that the recombinant vaccinia viruses that express gag, gag+env, or gag+env+pol polypeptides are capable of assembling into retroviral-like particles, lysate of cells infected with these recombinant vaccinia viruses were visually examined by electron microscopy by the methods detailed in the Materials and Methods section above.

These experiments showed that vaccinia recombinants that express gag, (vAbT141 or vAbT252) env+gag, (vAbT223, vAbT264 or vAbT344) or env+gag+pol (vAbT277) genes give rise to the formation of enveloped retroviral particles; in the recombinants that coexpress gag and env polypeptides, (vAbT223 vAbT264, vAbT344 and vAbT277) the particle envelope contains the envelope glycoproteins, as shown by the presence of glycoprotein "spikes" on the surface of the particles. For the SIV recombinant vAbT223, the presence of SIV envelope glycoproteins on the surface of the particles was also demonstrated with immunogold electron microscopy, using a monoclonal antibody directed against one of the envelope glycoproteins.

Plasmid Deposits

The plasmids *E. coli* MC1061 pAbT 4597 and *E. coli* MC 1061 pAbT621 were placed on deposit, under provisions of the Budapest Treaty, at the American Type Culture Collection in Rockville, Md. on May 31, 1989. The plasmids have been assigned the accession numbers 67998 and 67999, respectively.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A plasmid vector for insertion of lentivirus DNA sequences into a pox virus vector by in vivo recombination, the plasmid vector comprising:

(a) a prokaryotic origin of replication, so that the plasmid vector may be amplified in a prokaryotic host cell:

(b) a gene encoding a marker which allows selection of prokaryotic host cells that contain the plasmid vector;

(c) at least two DNA sequences from a single species of lentivirus, wherein one of the lentivirus DNA sequences is the gag gene and the other of the lentivirus DNA sequences is the pol gene, such that each gene is operably-linked to a separate eukaryotic transcriptional promoter capable of directing the co-expression of gag and pol proteins that self-assemble into a defective, non-self-propagating lentivirus particle; and (d) pox virus DNA sequences flanking (c), wherein the pox virus DNA sequences are homologous to a region of the genome of a pox virus vector to allow in vivo recombination between the plasmid vector and the pox virus vector, thereby inserting (c) into the pox virus vector.

2. The plasmid vector of claim 1, wherein the lentivirus is human immunodeficiency virus (HIV).

3. The plasmid vector of claim 1, wherein the lentivirus is simian immunodeficiency virus (SIV).

4. The plasmid vector of claim 1, wherein the pox virus DNA sequences of (d) are homologous to a non-essential region of the genome of pox virus vector.

5. The plasmid vector of claim 4, wherein the non-essential region is the thymidine kinase gene.

6. The plasmid vector of claim 4, wherein the pox virus vector is a vaccinia virus.

7. A plasmid vector selected from the group consisting of pAbT4597 and pAbT621.

8. A pox virus vector having inserted therein, at least two DNA sequences from a single species of lentivirus, wherein one of the lentivirus DNA sequences is the gag gene and the other of the lentivirus DNA sequences is the pol gene, such that the gag and pol proteins are expressed in a eukaryotic host cell infected with the pox virus vector, and the gag and pol proteins self-assemble into defective, non-self-propagating lentivirus particles.

9. The pox virus vector of claim 8, wherein the pox virus is a vaccinia virus.

10. The pox virus vector of claim 8, wherein the lentivirus DNA sequences are SIV DNA sequences or HIV DNA sequences.

11. A pox virus vector having inserted therein, two DNA sequences from a single species of SIV or HIV, wherein one of the DNA sequences is the gag gene and the other of the DNA sequences is the env gene, such that the gag and env proteins are co-expressed in a eukaryotic host cell infected with the pox virus vector, and the gag and env proteins self-assemble into defective, non-self-propagating SIV or HIV particles.

12. The pox virus vector of claim 11, wherein the two DNA sequences are from HIV.

13. A pox virus vector having inserted therein, three DNA sequences from a single species of HIV, wherein the first of the DNA sequences is the gag gene, the second of the DNA sequences is the pol gene and the third of the DNA sequences is the env gene, such that the gag, pol and env proteins are co-expressed in a eukaryotic host cell infected with the pox virus vector, and the gag, pol and env proteins self-assemble into defective, non-self-propagating HIV particles.

14. Two pox virus vectors, each pox virus vector having inserted therein only one of either of two DNA sequences from a single species of lentivirus, wherein one of the lentivirus DNA sequences is the env gene and the other of the lentivirus DNA sequence is selected from the group consisting of the gag gene and gag-pol gene from the same species of lentivirus, such that the lentivirus DNA sequence express either env and gag proteins, or express env and gag-pol proteins in a eukaryotic host cell co-infected with the two pox virus vectors, and the lentivirus proteins self-assemble into defective, non-self-propagating lentivirus particles.

15. A recombinant vaccinia virus which co-expresses, in eukaryotic cells, HIV gag and env genes, said virus being capable of expressing polypeptides capable of self-assembly into defective, nonself-propagating particles.

16. A vaccinia virus vector comprising a first and a second chimeric gene inserted within the HindIII M region of the vaccinia virus vector, wherein the first chimeric gene comprises and HIV env gene operably linked to the 40K vaccinia promoter, the second chimeric gene comprises an HIV gag-pol operably linked to the 30K vaccinia promoter such that the gag, pol and env proteins are co-expressed in a host cell infected with the pox virus vector, and the gag, pol and env proteins self-assemble into defective, non-self-propagating HIV particles.

17. A vaccinia virus vector selected from the group consisting of vAbT223, vAbT264, vAbT344, and vAbT277, such that lentivirus proteins are co-expressed in a eukaryotic host cell infected with pox virus vector, and the lentivirus proteins self-assemble into defective, non-self-propagating lentivirus particles.

18. A self-assembled, defective, non-self-propagating lentivirus particle produced by a eukaryotic host cell infected with the pox virus of claim 8.

* * * * *